United States Patent
Walk et al.

(10) Patent No.: US 8,190,375 B2
(45) Date of Patent: May 29, 2012

(54) SYSTEM AND METHOD FOR CHARACTERIZING A CHEMICAL SAMPLE

(75) Inventors: Tilmann B. Walk, Kleinmachnow (DE); Martin Dostler, Henningsdorf (DE)

(73) Assignee: Metanomics GmbH, Berlin (DE)

( * ) Notice: Subject to any disclaimer, the term of this patent is extended or adjusted under 35 U.S.C. 154(b) by 295 days.

(21) Appl. No.: 11/995,057

(22) PCT Filed: Jun. 30, 2006

(86) PCT No.: PCT/EP2006/063723
§ 371 (c)(1),
(2), (4) Date: Jan. 8, 2008

(87) PCT Pub. No.: WO2007/006661
PCT Pub. Date: Jan. 18, 2007

(65) Prior Publication Data
US 2008/0234948 A1    Sep. 25, 2008

(30) Foreign Application Priority Data
Jul. 8, 2005    (EP) .................................... 05014888

(51) Int. Cl.
*G01N 31/00* (2006.01)
(52) U.S. Cl. .......................................... 702/23; 702/22
(58) Field of Classification Search .................... 702/23, 702/22
See application file for complete search history.

(56) References Cited

U.S. PATENT DOCUMENTS

| | | | |
|---|---|---|---|
| 5,452,618 A | 9/1995 | Bülow et al. | |
| 6,140,638 A | 10/2000 | Tanner et al. | |
| 7,196,323 B2 | 3/2007 | Walk et al. | |
| 2004/0083063 A1* | 4/2004 | McClure | 702/22 |
| 2005/0127287 A1* | 6/2005 | Plumb et al. | 250/281 |

FOREIGN PATENT DOCUMENTS

| | | |
|---|---|---|
| WO | WO 01/15201 | 3/2001 |
| WO | WO-01/15201 A2 | 3/2001 |
| WO | WO 03/073464 | 9/2003 |
| WO | WO-03/073464 A1 | 9/2003 |
| WO | WO 2004/009390 | 1/2004 |
| WO | WO-2004/009390 A2 | 1/2004 |

OTHER PUBLICATIONS

Jonsson et al., Extraction, interpretation and validation of information for comparing samples in metabolic LC/MS data sets, *The Royal Society of Chemistry*, vol. 130, pp. 701-707 (2005).
Jonsson et al., "A Strategy for Identifying Differences in Large Series of Metabologmic Samples Analyzed by GC/MS", *Anal. Chem.*, vol. 76, pp. 1738-1745 (2004).
Bernal et al., "Energy spectra of laser-produced ions", *Journal of Applied Physics*, vol. 45, No. 7, pp. 2980-2986 (1974).

* cited by examiner

*Primary Examiner* — Janet Suglo
(74) *Attorney, Agent, or Firm* — Connolly Bove Lodge & Hutz LLP

(57) ABSTRACT

A method for characterizing a sample containing at least one compound is disclosed. Initially, a three-dimensional set of data is generated through sample analysis using time resolved and mass resolved separation techniques. The data comprises at least one signal as a function of a mass variable over a first range of measurement and of a time variable over a second range of measurement. The first range of measurement is divided into at least two mass variable intervals, and for each mass variable interval, an extracted signal is selected which is a function of the time variable. The second range of measurement is divided into at least one time variable interval. A characteristic value is then selected for each time variable interval and each extracted signal to generate a characteristic sample profile, comprising one or more characteristic values as functions of respective time variable intervals and respective mass variable intervals.

19 Claims, 7 Drawing Sheets

SYSTEM AND METHOD FOR CHARACTERIZING A CHEMICAL SAMPLE

RELATED APPLICATIONS

Figure 1:
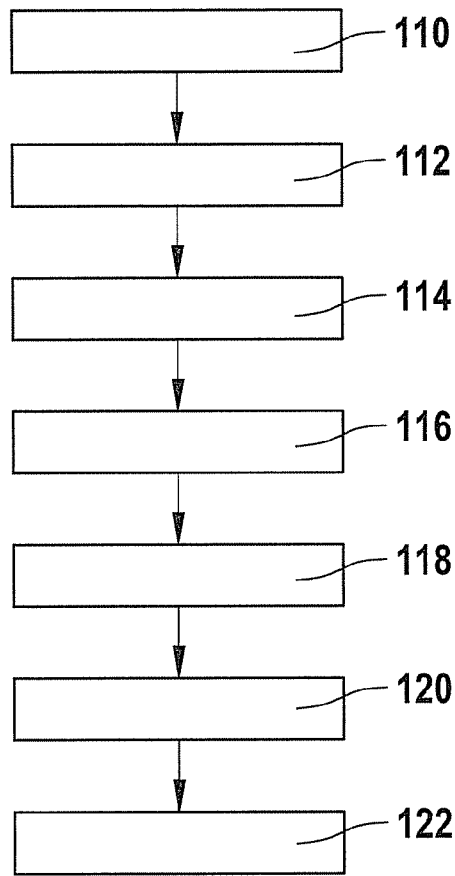

Priority is claimed as a national stage application under 35 U.S.C. §371 to PCT/EP2006/063723, filed Jun. 30, 2006, which claims priority to European application 05014888.1, filed Jul. 8, 2005. The disclosure of each application to which priority is claimed is incorporated herein by reference as if set forth in full.

FIELD OF THE INVENTION

The invention refers to a method for characterizing a sample containing at least one compound, preferably a biological sample. The method further discloses means for characterizing the sample, such as a system comprising means for performing the method according to the invention, as well as computer means and database means. The method and means are particularly suited for characterizing biological samples, such as samples comprising at least one metabolite.

PRIOR ART

For analyzing and/or characterizing chemical samples, a large variety of analytical techniques is known to the person skilled in the art. Among those techniques, mass spectrometry and chromatography are particularly wide-spread examples.

Mass spectrometry (MS) is a widely used method for identifying substances or molecules in the field of organic chemistry as well as in the field of inorganic chemistry. Ions are separated according to their mass-to-charge-ratio (m/z) and are detected. The detection of the separated ions may be performed using several techniques, such as using a photographic plate or electrical detection methods measuring an ion current. In the literature, the case of detection using a photo plate is sometimes referred to as "mass spectroscopy", and the latter case using an electrical detection of the ion current, is sometimes referred to as "mass spectrometry". Nevertheless, in the following, both methods and methods using other ion detection means will be referred to as "mass spectrometry".

A mass spectrometer typically comprises three major components: means for generating ions (ion source), means for separating ions (analyzer), and an ion detector, such as a Faraday cage, or a secondary electron multiplier. Additionally, an electronic control system, a computer system, as well as one or more vacuum pumps are typical components of mass spectrometers.

In some cases of characterization and/or analysis of chemical samples, two or more characterization techniques may be combined. Thus, over the recent years, a combination of mass spectrometry (MS) with several other methods of analysis has become popular. Thus, mass spectrometry may be combined with chromatographic methods, such as gas chromatography (GC) and/or liquid chromatography (LC). This combination is often referred to as "GCMS" or "LCMS", respectively. The combination of the experimental methods allows, e.g., for a separation of the sample using chromatography, followed by an analysis of the separated sample using mass spectrometry. Thus, highly efficient analytical systems may be designed, which, in a simplified way of speaking, generate a delayed arrival of the single components of the separated sample at the detector of the mass spectrometer and, thus, simplify the analysis of the sample. The number of the molecules and/or kinds of molecules and/or ions, which are, e.g., generated by ionization, re-organization, fragmentation etc., being present in the mass spectrometer at one time are reduced, and the separation of the mass spectra and ion intensity peaks as function of time, and matching those peaks with certain analytes (substances) is made possible or is greatly simplified.

Typically, results are obtained by integrating the chromatographic intensity peaks of the detector signal for single peaks or a plurality of peaks by using pre-defined methods. Characteristic criteria for detecting correct signals of the chromatogram or mass spectrum and for matching those signals to known chemical compounds are used, such as retention time (time lapsed between injection of the sample and corresponding signal peak) and/or additional information, such as the characteristic mass spectrum of the chemical compound, being detected by the detector at a specific retention time.

Nevertheless, an analysis using mass spectrometry and chromatography fails, when two or more components elute closely to each other, causing their retention times to differ minimally and, thus, causing the components entering the mass spectrometer simultaneously or nearly simultaneously. Further, analysis of the results becomes difficult or impossible if the number of compounds being present in the chemical sample rises and, at the same time, if mass spectra of analytes, which are incompletely separated by chromatography, differ only slightly or differ not at all. Typically, this situation occurs when analyzing waste water, toxic waste, organic and biologic tissue, such as plant extracts, i.e. in cases of typically more than 1000 compounds being present in the sample.

Additionally, the spectra obtained are often "impurified". These impurities may, e.g., be caused by a capillary column being used in the chromatographic apparatus (an effect often called "bleeding" of the column material), impurities in the ion chamber and/or inappropriate handling of the sample, such as a decomposition of the sample.

In those cases, computer programs and methods for searching libraries or databases of reference spectra and comparing those reference spectra with the experimental data are of little help.

A further major problem using analytical techniques combining chromatography and mass spectrometry is the amount of experimental data, which may be extremely large when extensive series of samples are evaluated. This problem is known from the literature, especially from projects working on metabolic signatures in biological samples, such as for building metabolic databases, which very often use LCMS (a combination of liquid chromatography and mass spectroscopy) for analyzing the biological samples. Thus, in Pär Jonsson et al: "Extraction, interpretation and validation of information for comparing samples in metabolic LC/MS data sets", Analyst, 2005, 130, 701-707, a method is described, which allows for creating robust and interpretable multivariate models for the comparison of many samples. The method described involves the construction of a representative data set, including automatic peak detection, alignment, setting off retention time windows, summing in the chromatographic dimension and data compression by means of alternating regression. The method allows for the comparison of large numbers of samples based on their LC/MS metabolic profiles.

Nevertheless, the method described by Jonsson et al. necessarily involves a step of alignment and peak detection as a process step. In many cases of real biological samples, this is a major drawback for the interpretation of data, since peak detection of LCMS data is not feasible in all cases and typically involves a high uncertainty of the data obtained. This is mostly due to the fact that the peak density in chromatographic data of biological samples in many cases is very high, rendering the separation of neighboring peaks rather difficult. Further, peaks may be "smeared out" by impurities in the sample or experimental artefacts. Thus, not all peaks are detected, and in some cases, even additional, artificial peaks are detected. Therefore, the set of variables obtained for one sample not necessarily represents the same metabolite in all other samples.

In Pär Jonsson et al: A Strategy for Identifying Differences in Large Series of Metabolomic Samples Analyzed by GC/MS", Analytical Chemistry, Vol. 76, No. 6, 2004, 1737-1745, a second method for identifying and quantifying metabolites in a biological system is described. The method includes baseline correction, alignment, time window determination, alternating regression, PLS-DA, and identification of retention time windows in the chromatograms that explain the differences between the samples. The use of alternating regression further gives interpretable loadings which retain the information provided by m/z values that vary between the samples in each retention time window. The method further involves summarizing the total intensity of the chromatograms of each m/z channel for each time window, resulting in a total mass spectrum for each time window. A disadvantage of said method is, however, that m/z information is lost. Specifically, although the total mass spectrum for all m/z channels in a time window may be identical, the peaks in each channel in a certain time window may differ. For example, for one sample analysis, a first m/z channel in a certain time window may contain a high peak and a second m/z channel may contain a low peak. In a second sample analysis, the peaks may occur vice versa. The samples in this case are, hence, different but will appear to be identical when applying the aforementioned method.

DISCLOSURE OF THE INVENTION

Therefore, the present invention relates to a method as well as means for performing this method, such as a computer program, a storage medium, a system for performing the method, and a database. The method allows for characterizing a sample containing at least one compound.

The term "sample" as used herein refers to artificial samples, biological samples or environmental samples. An artificial sample is a sample which comprises or consists of at least one pre-selected compound. The at least one pre-selected compound may be admixed with other compounds to yield the sample. Moreover, said compounds may be obtained as the result of various chemical reactions performed in vitro. Accordingly, the at least one compound in accordance with the present invention may be the product or a plurality of products obtained by a chemical reaction and to be characterized by the methods described herein below. Moreover, samples comprising at least one compound may be obtained from biological or environmental sources. Usually, biological samples from various sources comprise a plurality of compounds. They are, thus, complex samples which are difficult to analyze and to characterize. Biological sample as used herein includes samples from biological sources, such as samples derived from an organism. Organisms as used herein encompass animals (including humans), plants, bacteria, fungi and viruses. Samples of bacteria, viruses or fungi, preferably, are provided in form of cultures comprising them. How to provide and obtain such cultures is well known in the art. Samples from plants may be obtained from parts of the plants, such as their leaves, stems or flowers, or from their seeds. Moreover, the term includes primary cells or cell cultures. Samples from an animal include samples of body fluids, such as blood, plasma, serum, urine or spinal liquor, or samples derived, e.g., by biopsy, from cells, tissues or organs. Moreover, the term includes primary cells or cell cultures. Moreover, a sample in accordance with the present invention further includes environmental samples. Environmental samples are to be obtained from any suitable place of nature. They comprise, preferably, at least one compound present at said place of nature. More preferably, environmental samples comprise a plurality of compounds to be found at said place, such as organic and inorganic compounds or organisms. The aforementioned samples are, preferably, pre-treated before they are characterized by the method of the present invention. Said pre-treatment may include treatments required to release or separate the compounds, to remove excessive material or waste, or to provide the compounds in a form suitable for compound analysis. For example, if gas-chromatography coupled to mass spectrometry is used in the method of the present invention, it will be required to derivatize the compounds prior to the said gas chromatography. Suitable and necessary pre-treatments depend on the means used for carrying out the method of the invention and are well known to the person skilled in the art. Pre-treated samples as described before are also comprised by the term "sample" as used in accordance with the present invention.

The term "at least one compound" as used herein refers to a sample containing a single compound, i.e. consisting essentially of said single compound or to a sample which contains a plurality of compounds, i.e. preferably at least 5, 10, 50, 100, 500, 1000, 2000, 3000, 5000 or 10,000 different compounds. A compound in accordance with the present invention encompasses all classes of organic or inorganic chemical compounds including those being or being comprised by biological material such as organisms. Preferably, the compound in accordance with the present invention is a small molecule compound, more preferably a metabolite. The metabolites are small molecule compounds, such as substrates for enzymes of metabolic pathways, intermediates of such pathways or the products obtained by a metabolic pathway. Metabolic pathways are well known in the art and may vary between species. Preferably, said pathways include at least citric acid cycle, respiratory chain, photosynthesis, photorespiration, glycolysis, gluconeogenesis, hexose monophosphate pathway, oxidative pentose phosphate pathway, production and β-oxidation of fatty acids, urea cycle, amino acid biosynthesis pathways, protein degradation pathways such as proteasomal degradation, amino acid degrading pathways, biosynthesis or degradation of: lipids, polyketides (including e.g. flavonoids and isoflavonoids), isoprenoids (including eg. terpenes, sterols, steroids, carotenoids, xanthophylls), carbohydrates, phenylpropanoids and derivatives, alcaloids, benzenoids, indoles, indole-sulfur compounds, porphyrines, anthocyans, hormones, vitamins, cofactors such as prosthetic groups or electron carriers, lignin, glucosinolates, purines, pyrimidines, nucleosides, nucleotides and related molecules such as eg. tRNAs, microRNAs or mRNAs. Accordingly, small compound metabolites are preferably composed of the following classes of compounds: alcohols, alkanes, alkenes, alkines, aromatic compounds, ketones, aldehydes, carboxylic acids, esters, amines, imines, amides, cyanides, amino acids, peptides, thiols, thioesters, phosphate esters, sulfate esters, thioethers, sulfoxides, ethers, or combinations or derivatives of the aforementioned compounds. The small molecules among the metabolites may be primary metabolites which are required for normal all function, organ function or animal growth, development or health. Moreover, small molecule metabolites further comprise secondary metabolites having essential ecological function, e.g. metabolites which allow an organism to adapt to its environment. Furthermore, metabolites are not limited to said primary and secondary metabolites and further encompass artifical small molecule compounds. Said artificial small molecule compounds are derived from exogenously provided small molecules which are administered or taken up by an organism but are not primary or secondary metabolites as defined above. For instance, artificial small molecule compounds may be metabolic products obtained from drugs by metabolic pathways of the animal. Moreover, metabolites further include peptides, oligopeptides, polypeptides, oligonucleotides and polynucleotides, such as RNA or DNA. More preferably, a metabolite has a molecular weight of 50 Da to 30,000 Da (Dalton), most preferably less than 30,000 Da, less than 20,000 Da, less than 15,000 Da, less than 10,000 Da, less than 8,000 Da, less than 7,000 Da, less than 6,000 Da, less than 5,000 Da, less than 4,000 Da, less than 3,000 Da, less than 2,000 Da, less than 1,000 Da, less than 500 Da, less than 300 Da, less than 200 Da, less than 100 Da. Most preferably, a metabolite in accordance with the present invention has a molecular weight of 50 up to 1,500 Da.

The expression "characterizing", as shown below, preferably includes a large variety of means with different goals and/or results, such as generating a characteristic sample profile, which characterizes this specific sample. Thus, "characterizing" preferably includes the generation of a data set, which is specific to this individual sample. Further, the expression "characterizing" preferably includes a comparison of the sample with other samples, such as reference samples and/or samples of known composition, in order to generate information on similarities and/or differences between the sample and other samples. The latter also may include the generation of information on the presence of certain specific compounds in the sample. The characterization may also involve comparing the characteristic sample profile of the sample with reference profiles, such as profiles of known chemical compounds stored in a database. Further, analytical methods known from prior art, especially methods known from bioinformatics, may be used to further process the characteristic sample profile, in order to obtain, e.g., statistical information or other information, which shall also be included in the meaning of the expression "characterizing".

The method described in the following comprises a number of process steps. Nevertheless, these process steps shall not necessarily be performed in the order described below. Process steps may be performed in parallel or repetitively, and/or other process steps not listed below, may be added.

In a first process step, a three-dimensional first set of data, which is characteristic for the sample comprising at least one compound, is generated. A "three-dimensional" set of data not necessarily restricts the dimensionality of the data set to three. Thus, further "dimensions" may be added, such as by adding additional process parameters or experimental results or additional information. Thus, the dimensionality may be higher than three.

The three-dimensional first set of data is generated by analyzing the sample by using at least one time resolved separation technique and at least one mass resolved separation technique. Thus, the first set of data, which may also be called a set of "raw data", comprises at least one signal I (e.g., the second dimension) as a function of a mass variable over a first range of measurement (e.g., the third dimension) and of a time variable over a second range of measurement (e.g., the first dimension).

The at least one time resolved separation technique preferably comprises one or more experimental techniques generating an experimental signal as a function of a time variable. Thus, as already indicated above, the at least one time resolved separation technique comprises preferably at least one chromatographic technique. Generally, any chromatographic technique may be used, such as gas chromatography, liquid chromatography (preferably high performance liquid chromatography, HPLC), thin layer chromatography and/or affinity chromatography. Alternatively or additionally, other time resolved experimental techniques may be used, such as capillary electrophoresis. Further, the time resolution may be obtained by other methods, such as by a delayed or time-varying injection of the sample into an experimental apparatus. Other preferred techniques include ion mobility. A large number of experimental techniques for generating a time-varying experimental signal are feasible and known to the person skilled in the art and shall be included by the expression "time resolved separation technique". The expression "separation technique" does not necessarily restrict the techniques to experimental techniques physically separating the sample into a plurality of physical portions, but may as well comprise the meaning of indicating to the experimentalist that several portions, such portions comprising at least one compound, are present within the sample, by generating a signal dependent on a time variable.

The time variable may, first of all, be a time, such as a process time, e.g. the internal clock time of a computer being part of an experimental apparatus. In this case, the time resolved separation technique generates a signal as a function of time. In case a chromatography is used as preferably envisaged in accordance with the present invention, the time variable is preferably the retention time. Nevertheless, the expression "time variable" may be generalized to basically any variable indicating a progress of the experiment or the measurement. Thus, e.g., the expression "time variable" may as well include a position variable, which may be transformed into a process time by using a characteristic "velocity". Thus, e.g., when using a chromatographic column, the position of a certain compound (indicated, e.g., by a specific coloration within the column) may be transformed into a time, such as by comparing the position of the compound to the position of a solvent within the peak, which is dependent on the velocity of the solvent within the column. Moreover, it is to be understood that temperature, polarity, chemical nature of the stationary phase of the column material etc. will also have an influence. Other types of "time variables" indicating a progress of the experiment or the measurement are feasible and shall be included, such as a number of cycles of a process of known periodicity.

Similarly, the at least one mass resolved separation technique may comprise one or more experimental techniques of various kinds. Preferably, the mass resolved separation technique comprises mass spectrometry. Generally, all known mass spectrometry methods may be used, such as magnetic sector mass spectrometry, time-of-flight mass spectrometry, quadrupole mass spectrometry, and/or ion trap mass spectrometry, or any combination thereof or a combination with other mass resolved separation techniques. Similarly to the expression "time variable", the expression "mass variable" shall not be restricted to a mass, and, may comprise, e.g., a mass-to-charge-ratio m/z and/or other variables being derived from a mass.

Time resolved separation techniques, such as chromatographic techniques, as well as mass resolved separation techniques, such as mass spectrometry, are known to the person skilled in the art and shall not be described in further detail in this disclosure.

The first range of measurement and the second range of measurement may, e.g., be the respective full range of measurement of the experimental setup used for the respective separation technique. Alternatively, it may be a section of the full range of measurement of the respective setup or even a plurality of single sections of the full range of measurement.

In a second process step of the method according to the invention, the first range of measurement, which is the range of measurement of the mass resolved separation technique, is divided into at least two mass variable intervals. The length of these at least two mass variable intervals shall, in the following, be named Δm. Preferably, the at least two intervals are of equal length. Nevertheless, a different way of dividing the first range of measurement may be chosen, in which case the length of the intervals are $\Delta m_1, \Delta m_2, \ldots$, or generally $\Delta m_i$, wherein i denotes an identification number of the respective mass variable interval.

Preferably, the length Δm of the at least one mass variable interval (or, in case of a non-equal division of the first range of measurement, the length of the smallest interval) is chosen to be greater than or equal to mass peak width $R_{mz}$, which has also to be seen in context of mass accuracy (difference between measured and theoretical mass) of the at least one mass resolved separation technique. The mass peak width definition for Quadrupole and Time-of flight instruments is the full width at half maximum intensity (FWHM). If more than one mass resolved separation technique is used, $R_{mz}$ shall be the minimum mass peak width of this plurality of mass resolved separation techniques.

Further, it is preferred that the length Δm of the at least one mass variable interval is chosen to be smaller than the full length of the first range of measurement $L_{mz}$. This shall be the case for all mass variable intervals, even if a non-equal division of the first range of measurement is used.

In a preferred embodiment, Δm (or at least one of the length $\Delta m_i$) is chosen to be within a range of 0.01 to 5 atomic mass units (amu). The full length of the first range of measurement $L_{mz}$ preferably is a greater than 1 amu. In many cases, it is specifically preferred to choose the length Δm of the at least one mass variable interval to be 1 atomic mass unit. It has to be noted, as indicated above, that the expression "atomic mass unit" may as well comprise an elementary charge. Thus, e.g., when using mass spectrometry, an interval length Δm of one atomic mass unit per elementary charge (amu/z) is preferred.

The second process step of dividing the first range of measurement into at least two multivariable intervals, further comprises a selection of an extracted signal for each mass variable interval. The extracted signal is a function of the time variable. Thus, the three-dimensional first set of data, comprising a plurality of signals I as a function of the mass variable and the time variable, is reduced to a plurality of functions of the time variable only, one function for each of the at least two mass variable intervals.

Generally, the extracted signal for each mass variable interval may be chosen by a number of methods, whereby the (originally still three-dimensional) first set of data within each mass variable interval is reduced to one function of the time variable only. Many of those methods of data compression, reducing dimensionality, are known to the person skilled in the art. Nevertheless, it is preferred if the extracted signal for each mass variable interval is selected by at least one of the following methods:

integrating the signal I over the (respective) mass variable interval;
summing the signal I over the mass variable interval;
averaging the signal I over the mass variable interval;
selecting the signal I at one of the interval boundaries of the mass variable interval;
selecting the maximum or minimum value of the signal I over the mass variable interval.

Other methods for selecting the extracted signal are feasible, such as selecting the signal I at a pre-determined point in between the mass variable interval boundaries. Which method for choosing the extracted signal is used, usually depends on a number of factors. In many cases, it is especially preferred to use a method of integration or summing. Integration is preferred in case I is a continuous signal, whereas summing is preferred if the signal I comprises a plurality of discrete values.

Thus, the originally three-dimensional first set of data is reduced to a plurality of at least two extracted signals, one for each of the at least two mass variable interval. It has to be understood, that throughout this disclosure, the expression "function" is not restricted to continuous functions, but may as well comprise discrete functions and discontinuous functions (e.g. centroid data).

After performing this second process step and, thus, after generating a plurality of at least two extracted signals, in a third process step, the second range of measurement, which is the range of measurement of the at least one time resolved separation technique, is divided into at least one time variable interval. Preferably, more than one time variable interval is used, such as ten time variable intervals.

In the following, the length of the at least one time variable interval shall be referred to as Δrt. As in the case of the length of the at least two mass variable intervals, the division of the second range of measurement into the at least one time variable interval preferably is performed by generating equal time variable intervals. Nevertheless, a non-equal division of the second range of measurement may be used alternatively.

Preferably, the length of the at least one time variable interval (or, in case of a non-equal division, the length of the shortest time variable interval) is chosen to be greater or equal to the cycle time of the at least one time resolved separation technique (or the minimum cycle time of the technique) or the minimum time interval within which two distinct peaks are resolvable using the at least one time resolved separation technique. Thus, if a time resolved separation technique of a cycle time (time for one measurement) of 100 milliseconds is used, the at least one time variable interval is chosen to be greater or equal than 100 milliseconds. Alternatively, if the minimum resolution time, which is the time within which two distinct peaks in the signal are resolvable using the at least one time resolved separation technique is known to be 1 second, the at least one time variable interval Δrt may be chosen to be greater or equal than 1 second. This minimum time interval may be calculated from the peak capacity $n_c$ reflecting the number of peaks which can be resolved in a lining-up of peaks on a defined spacing. which is known to the person skilled in the art and is, e.g., described in L. S. Ettre: "Grundbegriffe und Gleichungen der Gaschromatographie", Hüthig, Heidelberg, 1995, page 103-104. The peak capacity is calculated from $$n_c = 1 + \frac{\sqrt{N}}{4} \cdot \ln\frac{L_{rt}}{t_M},$$

with $$N = 16\left(\frac{t_R}{w}\right)^2 \quad N: \text{number of theoretical plates}$$

For example: $L_{rt}$ full range of chromatographic measurement=6 minutes $t_M$: holdup time of the chromatographic system=0.5 minutes
$t_R$: retention time of a certain chromatographic peak=1.0 minutes
w: chromatographic peak width at peak base of a certain peak=0.1 minutes resulting in $n_c$=25.8. Thus the minimum interval being 6 minutes/25.8=14 seconds.

Similarly, the at least one time variable interval (or the longest of these intervals, respectively) shall be chosen to be smaller or equal to the full length of the second range of measurement.

Followingly, within the third process step, at least one characteristic value is selected for each time variable interval and for each extracted signal. This characteristic value is selected, in order to characterize the respective extracted signal within the respective time variable interval, and, thus, reduces the dimensionality of the extracted signal from being a function of the time variable to the at least one characteristic value, similarly to the selection of the extracted signal for each mass variable interval as described above. As for the selection of the extracted signal, a number of methods reducing dimensionality may be used and are known to the person skilled in the art. These methods of data compression may, preferably, comprise one of the following methods:

integrating the extracted signal over the time variable interval;
summing the extracted signal over the time variable interval;
averaging the extracted signal over the time variable interval;
selecting the extracted signal at one of the interval boundaries of the time variable interval;
selecting the maximum or minimum value of the extracted signal over the time variable interval.

As in the case of the selection of the extracted signal for each mass variable interval, an integration is most preferred. In accordance with the present invention, it has been found that applying integration is particularly useful to generate the at least one characteristic value. Specifically, it has been found that such a characteristic value is highly informative and specific for a sample. Therefore, sample comparison based thereon is highly reliable.

Thus, by selecting the at least one characteristic value for each time variable interval and for each extracted signal, a characteristic sample profile is generated. This characteristic sample profile, characterizing the sample containing the at least one compound, comprises the at least one characteristic value as a function of the respective time variable interval and of the respected mass variable interval. Thus, since at least two mass variable intervals are used, and since at least one time variable interval is used, the characteristic sample profile comprises at least two characteristic values, one for each mass variable interval. This characteristic sample profile may thus be an at least two-dimensional matrix of characteristic values, at least one for each time variable interval and for each mass variable interval. Thus, the first set of data ("raw data"), characterizing the sample containing at least one compound, is reduced to the characteristic sample profile.

The method according to the invention as disclosed in one of the embodiments described above, provides a number of advantages over methods known from prior art. Thus, the method avoids the necessity of peak detection, which, as indicated above, is a disadvantage of many known methods. The position and the height of the peaks in the spectra, which is often used in prior art methods, may be replaced, e.g., by an integration over the time variable intervals. Thus, no time-consuming peak detection algorithm is necessary, and the above-mentioned uncertainties of peak detection are circumvented.

Further, the amount of data, starting from the first set of data ("raw data") may be significantly reduced by generating the characteristic example profile. This allows for a reduction of storage space, e.g. for storing the characteristic sample profile in a database. Further, the significant reduction of the amount of data may result in an easier further processing of the data, such as for the purpose of comparing two or more different samples by comparing their respective characteristic sample profile. Further advantages will become clear within the further description given below.

The characteristic sample profile characterizing the sample containing the at least one compound may be used in various ways, in order to further characterize the sample. Thus, the method according to the invention may be extended by adding a process step, in which the characteristic sample profile of the sample is compared with at least one characteristic sample profile of a second sample and/or with at least one reference sample profile. The second and/or reference sample is, preferably, a sample of a known composition or having at least a known characteristic. Said sample may be a real sample or a virtual sample. The virtual sample is merely information of the sample which is stored in a suitable format, e.g. in a matrix, for the purpose of comparison. The step of comparison of the characteristic sample profiles may be performed in various ways, which are known to the person skilled in the art. Thus, the comparison may be performed by using (e.g. commercially available) data analysis algorithms and, e.g., may be performed in view of other parameters of the sample or the samples. Thus, information on the sample containing at least one compound may be additionally stored, in combination with the characteristic sample profile. This information may contain information on sample preparation, pre-treatment of the sample, interrelations between samples, etc. The expression "comparing" may include a one-to-one comparison of the respective characteristic values of the characteristic sample profiles of the sample and the second sample and/or the reference sample, such as a comparison of the at least one characteristic value for one specific time variable interval and one specific mass variable interval with the corresponding characteristic value of the characteristic sample profile of the second sample and/or the reference sample. Thus, a difference between the characteristic values may be generated and/or a ratio of the characteristic values. Alternatively or additionally, a quotient of corresponding characteristic values may be formed, or any other algorithm comparing values. Depending on the second or reference sample used for the comparison it will be possible to determine, within a certain statistical likelihood, whether a sample is identical with a second sample or reference sample or differ therefrom. The term "identical" accordingly refers to a statistical degree of identity for the characteristic values which have been compared to each other. The same applies mutatis mutandis per the term "differ".

This comparison may be performed in order to determine whether the sample containing the at least one compound and the second sample or the reference sample are likely to be identical or are likely to comprise one or more identical or similar compounds. This determination may be performed qualitatively and/or quantitatively. Thus, it may be determined if the samples are likely to be identical or are likely to comprise one or more identical or similar compounds and/or, in case one or more identical or similar compounds are identified, a ratio of the quantities of these compounds within the sample may be determined. In many cases, statistical information is gained, such as when characterizing a large number of samples.

For the comparison of the sample containing the at least one compound and the second sample and/or the reference sample, several algorithms may be used as indicated above. These algorithms are known to the person skilled in the art. Nevertheless, it is preferred if the algorithm comprises a pattern recognition algorithm and/or a statistical test algorithm and/or a multivariate algorithm eg. Principal Component Analysis (PCA), Simple Component Analysis (SCA), Independent Component Analysis (ICA), Principal Component Regression (PCR), Partial Least Squares (PLS), PLS Discriminant Analysis (PLS-DA), Support Vector Machines (SVM), Neural Networks, Bayesian Networks, Bayesian Learning Networks, Mutual Information, Backpropagation Networks, symmetrical Feed-Forward Networks, Self-Organizing Maps (SOMs), Genetic Algorithms, Hierarchical or K-Mean Clustering, Anova, Student's t-Test, Kruskal-Wallis Test, Mann-Whitney Test, Tukey-Kramer Test or Hsu's Best Test.

The described comparison of the characteristic sample profile of the sample containing the at least one compound with the second sample and/or the reference sample may, depending on the details of the generation of the characteristic sample profile, be rather "crude". Thus, if only a small number of time variable intervals and/or mass variable intervals is chosen, the first set of data ("raw data") is reduced significantly to a sample profile comprising only a small number of characteristic values. Thus, the comparison of the characteristic sample profile of the sample containing the at least one compound with the second sample and/or the reference sample only may result in a first indication that the samples are likely to be identical or are likely to comprise one or more identical or similar compounds. This information may be used as a first step for pre-selecting or pre-matching samples or identifying certain known compounds within the sample.

Nevertheless, the method according to the invention may be further "refined" by adding a more detailed step of comparison, following to the described comparison of the characteristic sample profiles. Thus, in a following step, the three-dimensional first set of data or a relevant part thereof of the sample may be compared to a three-dimensional first set of data of the second sample or of the reference sample. A relevant part of the data set refers to a subset of data based on which the characteristic value can be determined or which represents the characteristic value. Thus, further clarification may be obtained on whether the samples are likely to be identical and/or are likely to comprise one or more identical or similar compounds. Thus, the comparison of the characteristic sample profiles may be used to reduce a large number of samples (e.g. several thousand samples) to a small group of samples which are likely to not match or to differ from a reference sample. Followingly, a more detailed comparison of the raw data may be performed, in order to further characterize the samples.

In this more detailed step of comparison, in which the raw data of the sample comprising the at least one compound and the second sample and/or the reference sample are compared, additional parameters may be used, in order to further compare the sample containing the at least one compound and the second sample and/or the reference sample. Thus, the abovementioned information on sample preparation and/or information on sample origin or other information may be used. Additionally, a peak detection and/or validation algorithm may be used in order to detect and/or validate peaks in the extracted signal within each time interval or peaks within the raw data (e.g., commercially available programs, such as ChemStation, (Agilent Technologies, USA) or AMDIS, (NIST, USA). Peaks can be also determined by comparison to available databases. Since, in this case, the peak detection algorithm is used as a "secondary" source of information only, the disadvantages of the peak detection algorithm are of minor importance. Thus, as an additional information, peaks within the extracted signals of the sample containing the at least one compound and the second sample and/or the reference sample may be used to further compare the samples.

Thus, the method according to the invention in one of the embodiments as described above allows for a fast comparison of a large number of samples by using a "pre-matching" step, followed by an optional step of a more detailed sample comparison. Thus, the time needed for comparing a large amount of samples is significantly reduced, and the necessity of extensive hardware resources is minimized.

Furthermore, the present invention includes a database comprising at least one characteristic sample profile generated by the method according to one of the embodiments described above. This database may be a single database and/or a combination of several databases linked to each other. As indicated above, the database may comprise additional information and parameters, such as information on the samples, sample pre-treatment etc. as well as information on the experimental methods, e.g. information on the means and parameters of the at least one time resolved separation technique and the at least one mass resolved separation technique. Further, the database may comprise relational information, such as information linking several samples (e.g. information that a group of biological samples is taken from a population of the same local area) or other relational information.

The invention further refers to a computer program comprising program code means for performing the method according to one of the embodiments described above while the computer program is being executed on a computer or on a computer network. Specifically, the program code means may be stored on a storage medium readable to a computer or a computer network.

Further, the invention refers to a storage medium, wherein a data structure is stored on the storage medium and wherein the data structure is adapted to perform the method according to one of the embodiments described above after having been loaded into a main storage and/or working storage of a computer or of a computer network. Further, the invention includes a computer program product having program code means, wherein the program code means can be stored or are stored on a storage medium, for performing the method according to one of the embodiments described above, if the program code means are executed on a computer or a computer network. In this context, a computer program product refers to the program as a tradable product. It may generally exist in arbitrary form, such as on paper or on a computer-readable storage medium, and may be distributed via a computer network.

DESCRIPTION OF PREFERRED EMBODIMENTS

Further details and characteristic features of the invention will become clear from the following description of preferred embodiments in combination with the dependent claims. Therein, the respective characteristic features may be realized by oneself or in combination with other characteristic features. The invention is not restricted to the embodiments.

Figure 2:
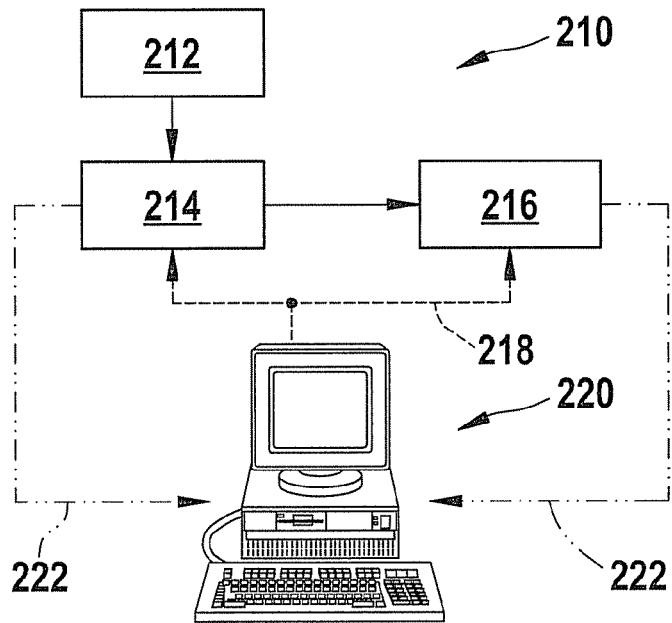
Figure 3:
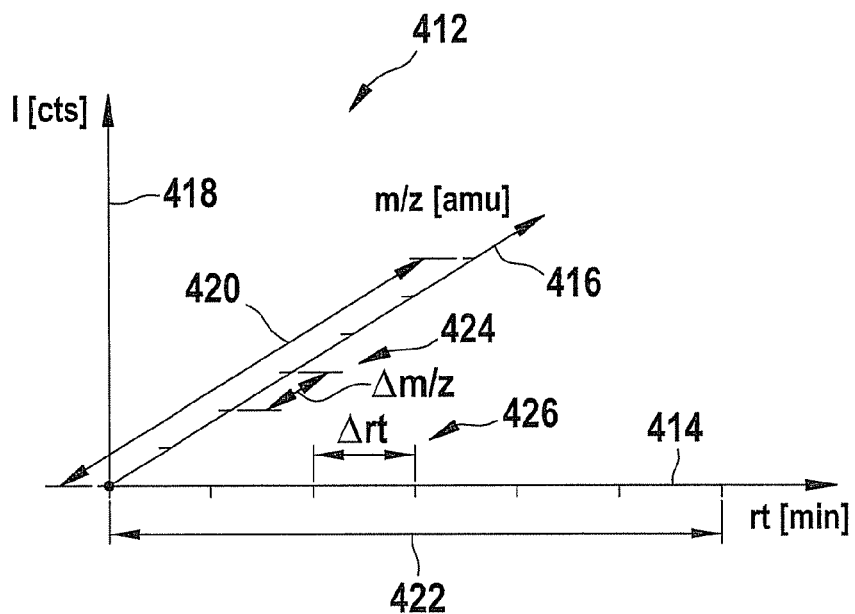
Figure 4:
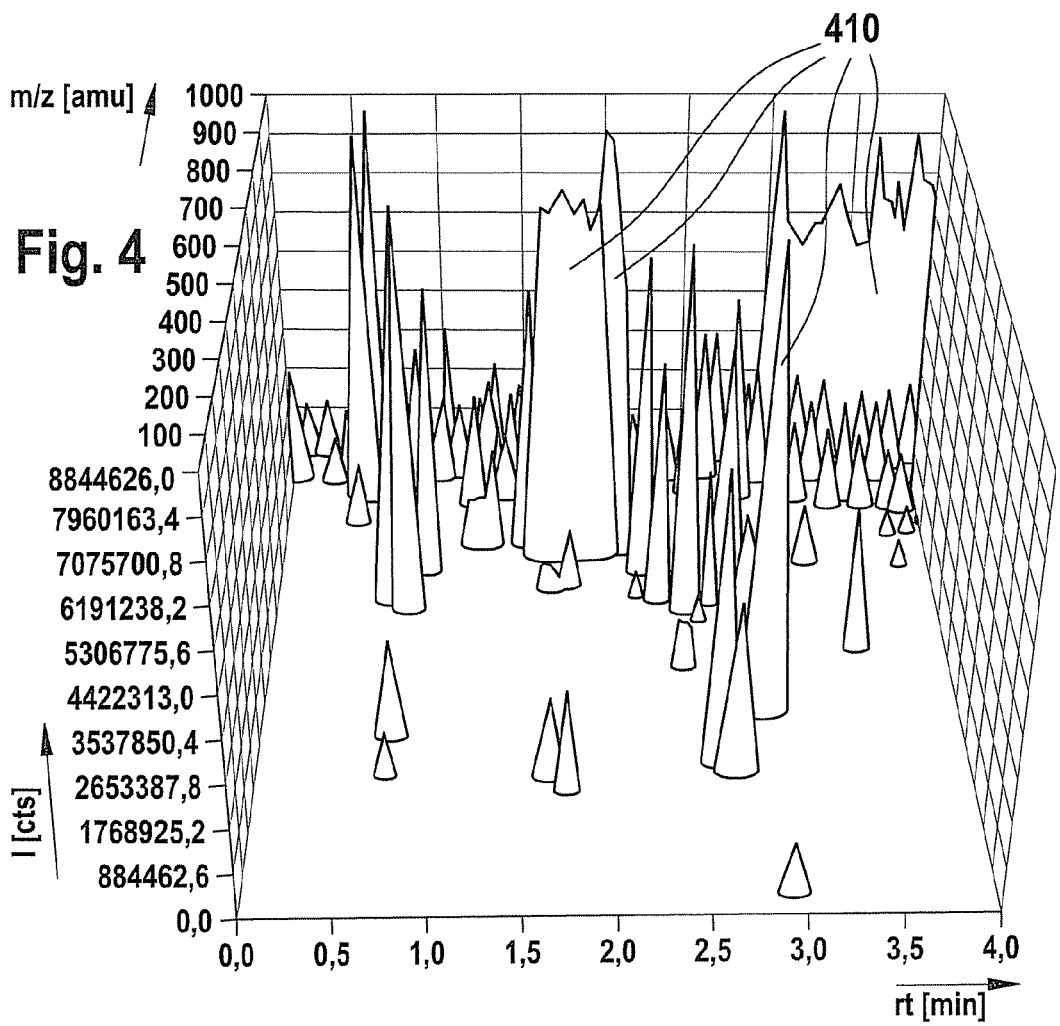
Figure 5:
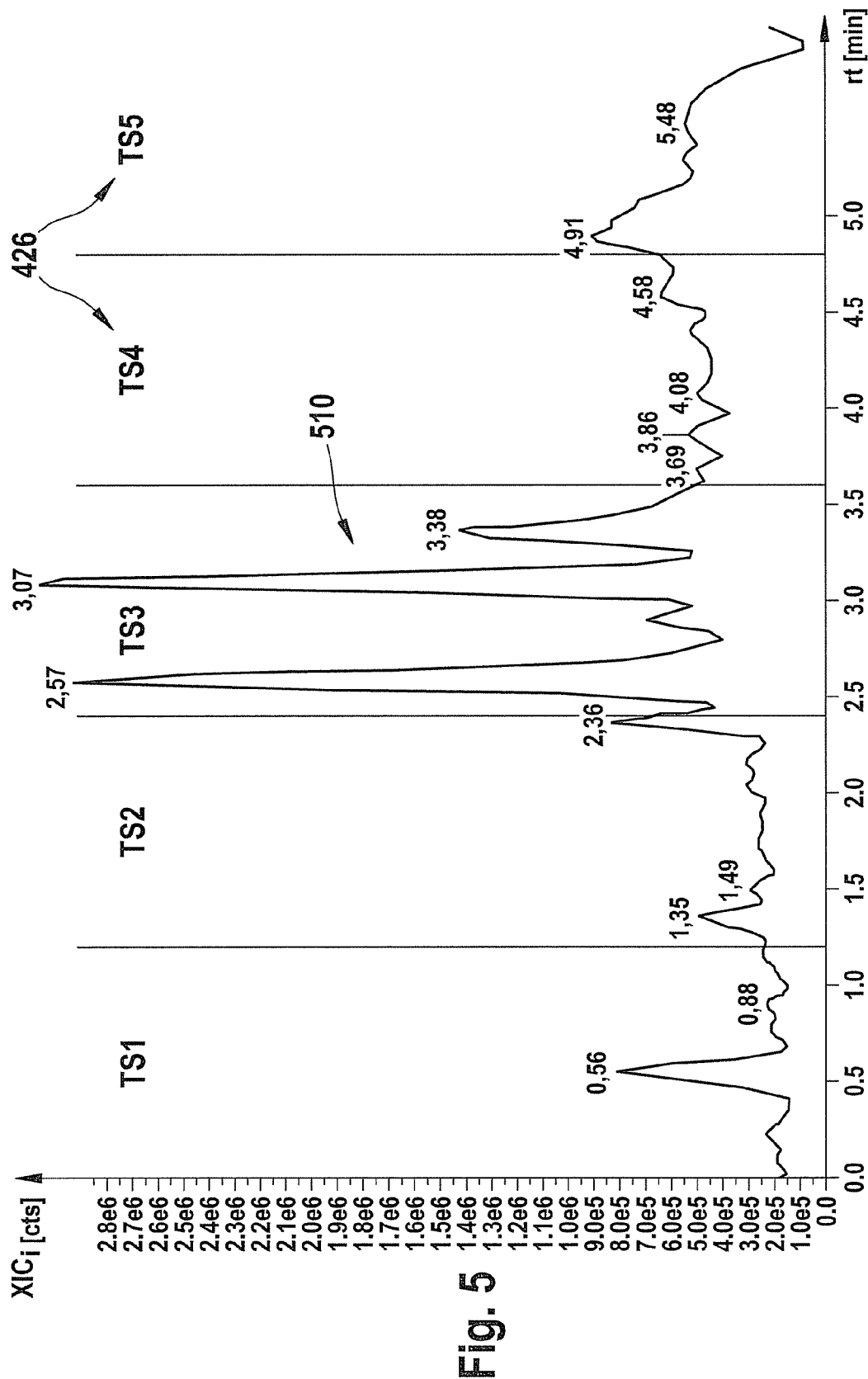
Figure 6:
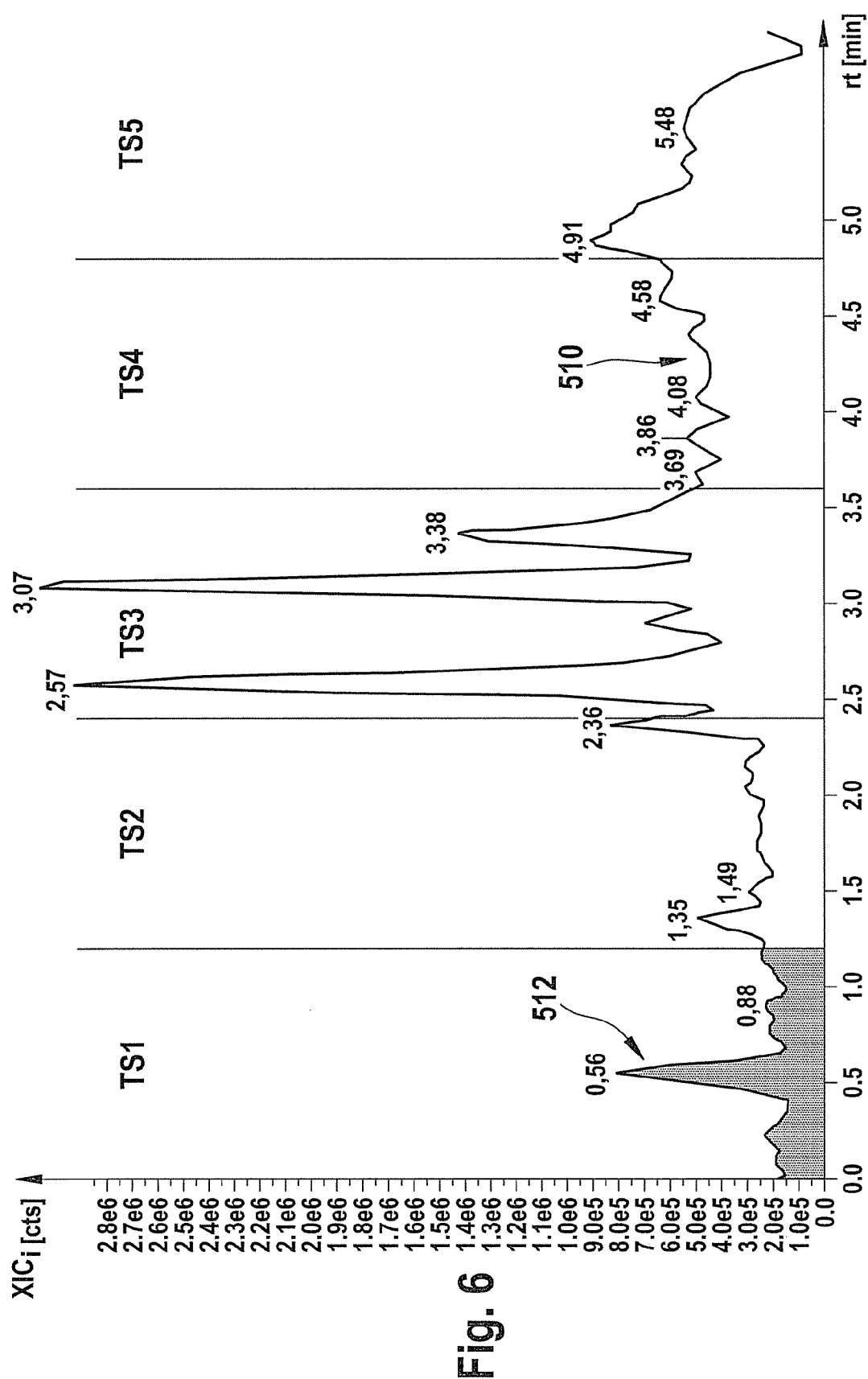
Figure 7:
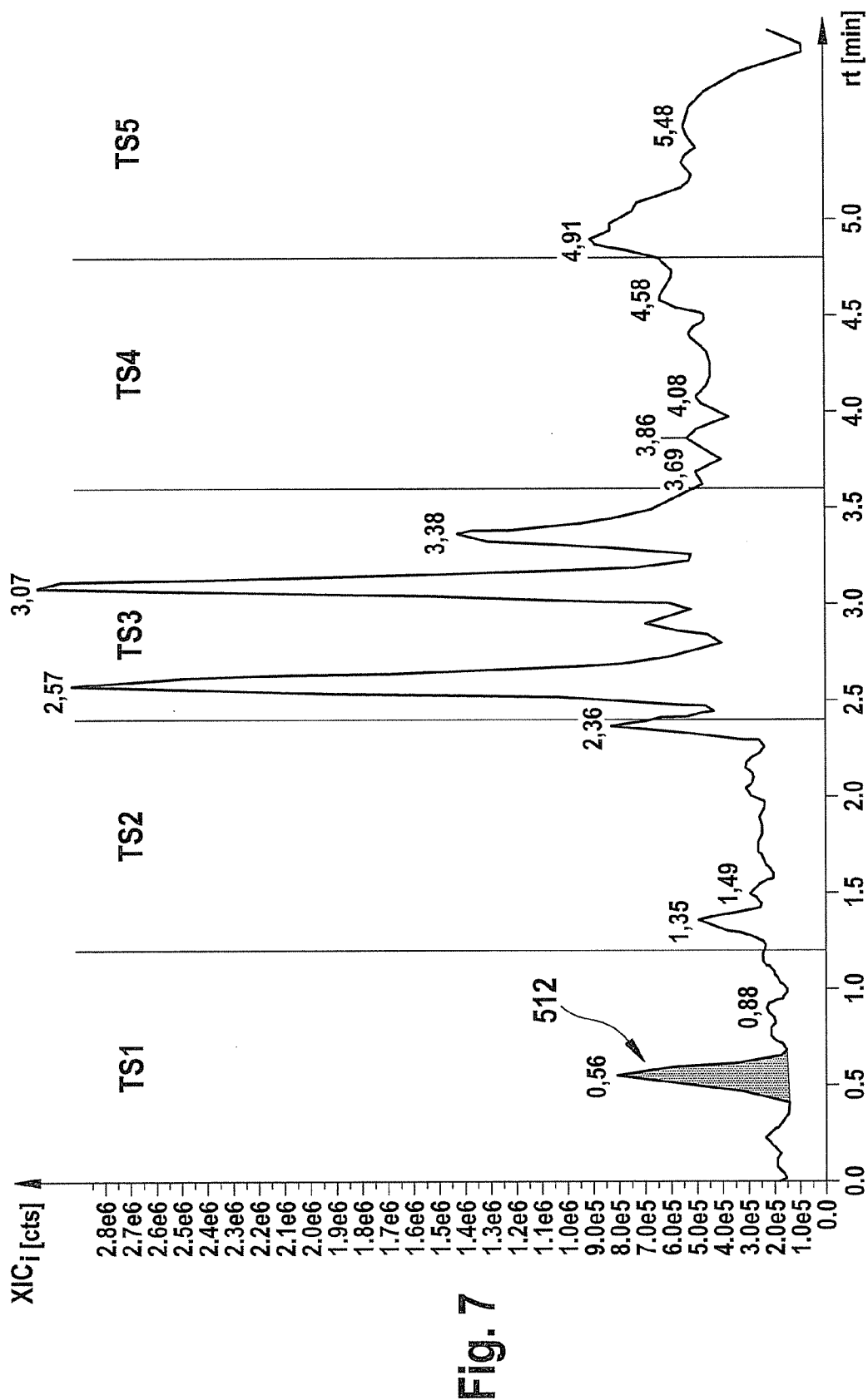

The embodiments are depicted schematically in the figures. Identical reference numbers in these figures denote identical or functionally similar or corresponding elements. The figures show:

FIG. 1 a preferred embodiment of the method according to the invention;

FIG. 2 a schematic setup of a preferred embodiment of a system for performing the method according to FIG. 1;

FIG. 3 a coordinate system of a three-dimensional first set of data characterizing a sample containing at least one compound;

FIG. 4 an example of a three-dimensional first set of data;

FIG. 5 an example of an extracted signal for one specific mass variable interval;

FIG. 6 the generation of a characteristic value of the first time variable interval of the example according to FIG. 5; and FIG. 7 an example of a peak integration algorithm according to the prior art.

Figure 8:
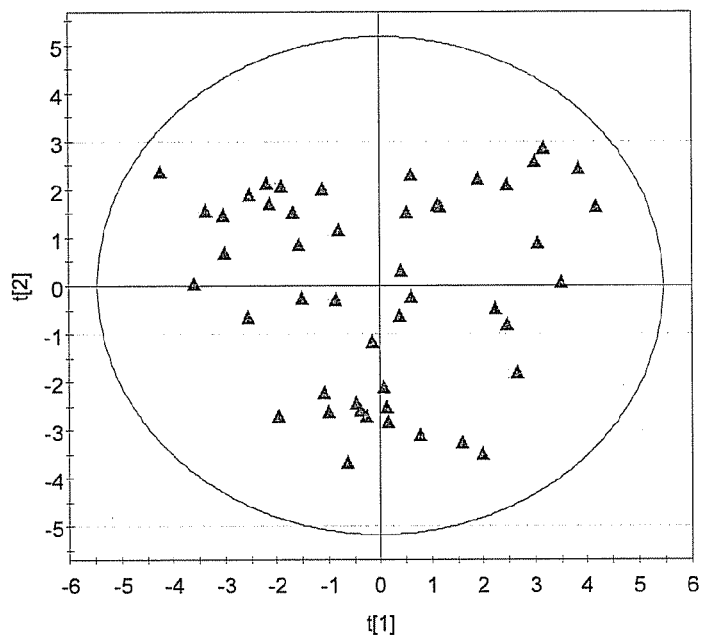
Figure 9:
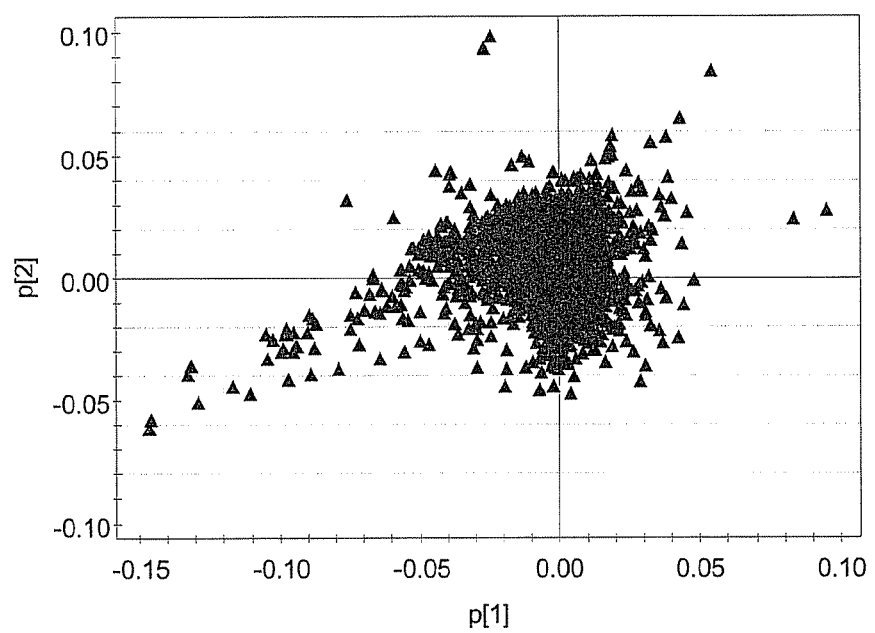
Figure 10:
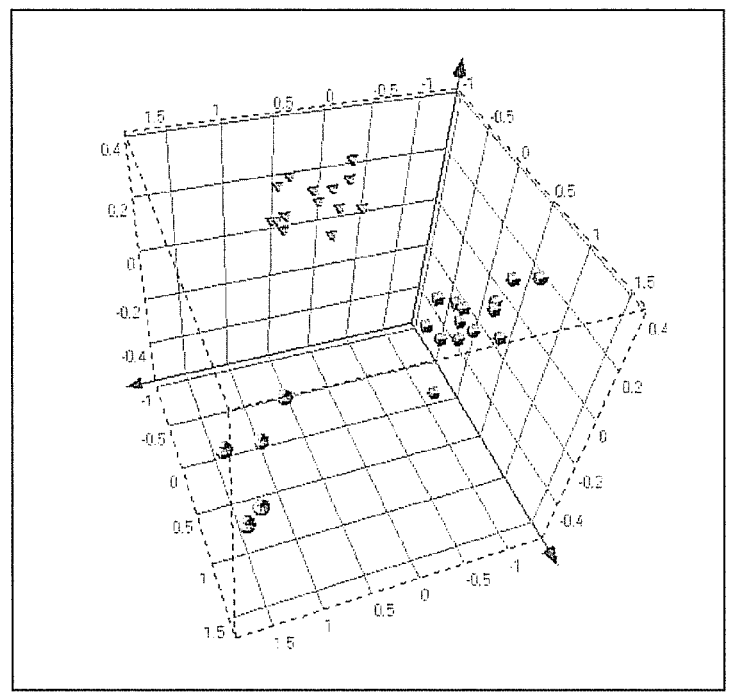

FIG. 8 a first example of the quality control as part of process step 120: sample level FIG. 9 a second example of the quality control as part of process step 120: variable level FIG. 10 a first example of the multivariate analysis as part of process step 122 3-dimensional visualisation of the results of a principal component analysis (PCA) based on an anova pre-selection of variables (slices); analysis based on blood plasma from rats subjected to different medications: untreated control rat (tetrahedrons), treatment-1 (spheres), treatment-2 (cubes), the axis represent the first three scores/principal components (t-1, t-2 and t-3)

Figure 11:
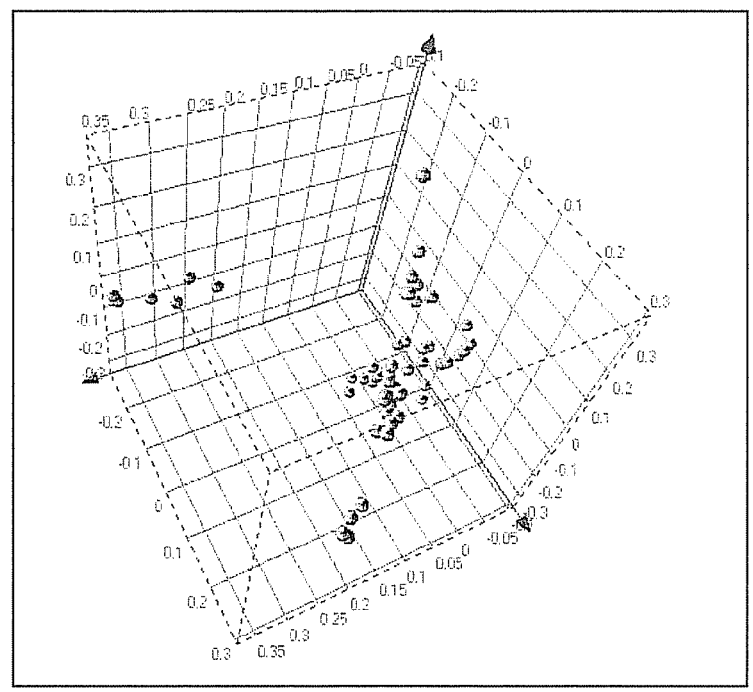

FIG. 11 a second example of the multivariate analysis as part of process step 122 3-dimensional visualisation of the loadings corresponding to the analysis shown in FIG. 10, the axis represent the first three loadings (p-1, p-2 and p-3)

In FIG. 1, a preferred exemplary embodiment of a method for characterizing a sample containing at least one compound is depicted. The method may be performed using a system 210 for characterizing a sample containing at least one compound, a preferred exemplary embodiment of which is depicted in FIG. 2. In the following, the process steps of the method according to FIG. 1 will be explained with respect to the system 210 according to FIG. 2.

In a first process step (step 110 in FIG. 1), a three-dimensional first set of data is generated by analyzing the sample. This first process step 110 comprises a large number of sub-steps, such as sample preparation, measurement and storage of the raw data in a database. The sample preparation symbolically is referred to by reference number 212 in the system 210 according to FIG. 2. In the following, it is assumed that the sample comprising at least one compound is a biological sample, wherein said compound is a metabolite. Thus, e.g., the sample may be a urine sample of one individual rat out of a rat population.

The sample is prepared in the following way: Proteins were separated by precipitation from blood plasma. The remaining plasma was fractioned into an aqueous, polar phase and an organic, lipophilic phase. Afterwards, the sample is inserted into a liquid chromatography system 214, which is coupled to a quadrupole mass spectrometry system 216. Thus, the sample is first separated by using the time resolved separation technique of liquid chromatography (LC), followed by the mass resolved separation technique of a mass spectrometry. Both systems 214, 216 are controlled (reference number 218) by a computer system 220, which controls the mass spectrometry system 216 as well as the liquid chromatography system 214 and reads out experimental data and system parameters (reference number 222).

The LC part was carried out on a commercially available LCMS system from Agilent Technologies, USA. For polar extracts 10 μl are injected into the system at a flow rate of 200 μl/min. The separation column was maintained at 15° C. during chromatography. For lipid extracts 5 μl are injected into the system at a flow rate of 200 μl/min. The separation column was maintained at 30° C.

The mass spectrometric analysis was performed on a Applied Biosystems API 4000 triple quadrupole instrument with turbo ion spray source. For polar extracts the instrument measures in negative ion mode with ion spray setting 4000 V, gas 1 35 psi, gas 2 30 psi, curtain gas 20 psi and temperature 600° C. The instrument is scanning in fullscan mode from 100-1000 amu in 1 second in fast profile mode with a mass dependent declustering potential starting from −30V to −100V. For lipid extracts the instrument measures in postive ion mode with ion spray setting 5500 V, gas 1 25 psi, gas 2 50 psi, curtain gas 25 psi and temperature 400° C. The instrument is scanning in fullscan mode from 100-1000 amu in 1 second in fast profile mode with a mass dependent declustering potential starting from 20V to 110V.

Thus, by using the system 210, for each sample a three-dimensional first set of data is generated, which contains a signal (intensity, counts) as a function of a mass-to-charge ratio m/z and as a function of the retention time of the liquid chromatography system 214.

An example of the three-dimensional first set of data of a biological sample is depicted in FIG. 4. It can be seen that the raw data contains a number of intensity peaks 410 rising from a horizontal plane. The axes of the data according to FIG. 4 are symbolically depicted in FIG. 3. Thus, the set of axes 412 comprises a retention time axis 414 (denoted by "rt"), wherein the units are minutes. Further, the set of axes 412 comprises a mass-to-charge axis 416, denoted by "m/z", wherein the units are atomic mass units (amu), which actually means "one atomic mass unit per elementary charge". The third axis of the orthogonal set of axes 412 is the signal axis 418, which is denoted by "I" in FIG. 4, wherein the units of the signal axis 418 are, in this example, counts.

Thus, the signal I is a function of the retention time rt and the mass-to-charge ratio m/z. The signal I, in this case, is a discrete function, comprising one signal data point per (MS mass spectrometry) measurement cycle. Nevertheless, as can be seen in FIG. 4, the experimental cycles are small enough with respect to the full range of measurement that the signal I is "smooth" rather than exhibiting discrete steps. Nevertheless, it has to be kept in mind that in reality the signal I is a discrete function, which means, that, when using "integration", in fact a summing of discrete data points is meant.

Further, in FIG. 3, a first range of measurement 420 is depicted, which denotes the range of measurement of the mass spectrometry. Further, a second range of measurement 422 is depicted, which denotes the range of measurement for the chromatography. Thus, mass spectrometry may be performed from, e.g., 100 atomic mass units per elementary charge to 1000 atomic mass units per elementary charge, e.g., in discrete steps of, e.g., 0.2 atomic mass units per elementary charge. Similarly, the second range of measurement 422 may be a range from 0.1 minutes to 6 minutes, in discrete steps of measurement (cycle time) of 1, 2 or 3 second, whereby 1 second is most preferred.

As it is further depicted in FIG. 3, the first range of measurement 420 and the second range of measurement 422 are divided into (in this example) equal intervals 424, 426. Typically, a mass variable interval 424 of a length Δm/z of 1 atomic mass unit is preferred, and, for a second range of measurement of 6 minutes, a time variable interval 426 of approximately Δrt=15 to 80 seconds is preferred, (ZEITINTERVALL BREITER DEFINIEREN, 5 TIMESLICES sind 72 seconds pro slice) which results in a preferred number of time variable intervals 426 of approx. 5 to 24. More preferably, Δrt=15 to 20 seconds Preferably, 1 to 20 time variable intervals 426 are used. As noted above, other embodiments of the division of the mass-to-charge axis 416 and of the retention time axis 414 are possible.

In a second process step (step 112 in FIG. 1), an extracted signal (often called extracted ion chromatogram, XIC) is selected for each of the mass variable intervals 424 of the raw data according to FIG. 4. In other words, this step comprises a compression of all raw data within one specific mass variable interval Δm/z 424, in order to assign one specific intensity for the specific mass variable interval 424 and for one specific retention time rt. This may, e.g., be done by summing up all intensity signals of the signal I for each retention time for each of the mass variable intervals 424. Thus, e.g., if the mass variable interval 424 referenced to in FIG. 3, is the $i^{th}$ mass variable interval, the extracted signal $XIC_i$ for this $i^{th}$ mass variable interval 424 is:

$$XIC_i(rt) = \Sigma_{\Delta m/z, i} I(rt, m/z). \quad (1)$$

Therein, "Δm/z, i" denotes a summing over the $i^{th}$ mass variable interval. Thus, the original three-dimensional first set of data I(rt, m/z) is reduced to a plurality of two-dimensional extracted signals $XIC_i$, which are a function of the retention time only. The number of extracted signals $XIC_i$ corresponds to the number of mass variable intervals 424. E.g., if mass variable intervals Δm/z of 1 atomic mass unit per elementary charge are used for a range of measurement from 100-1000 amu/z, there is one extracted signal XIC for amu/z=1, one extracted signal for amu/z=101-102, . . . and finally one extracted signal for m/z=999-1000 amu/z. As mentioned above, alternatively to integrating or summing, other methods may be used in order to obtain an extracted signal $XIC_i$ for each mass variable interval 424, such as, e.g., averaging, maximizing or minimizing.

In FIG. 5, an example of an extracted signal $XIC_i$ is depicted. As can be seen, the vertical XIC-axis has the units "counts", as is the case for the I-axis 418 in FIG. 3. The extracted signal 510 is a function of the retention time rt (horizontal axis), which is, in this example, given in minutes.

In a next process step, step 114 in FIG. 1, the retention time axis in FIG. 5 is divided into time variable intervals 426, which are symbolically denoted by "TS 1", "TS 2", . . . , "TS 5" in FIG. 5. In this example, in which the full second range of measurement 422 for a retention time axis 414 is 6 minutes, five time variable intervals are separated, each of a length of 72 seconds. These time variable intervals 426 are often referred to as "time slices".

After dividing the second range of measurement 422 into time variable intervals 426, in a further sub-step of process step 414 in FIG. 1, a characteristic value is selected for each time variable interval 426 of the extracted signal $XIC_i$. This process is depicted symbolically in FIG. 6. In this exemplary embodiment, the characteristic values are chosen by a simple integration of the extracted signal $XIC_i$ over the $j^{th}$ time variable interval. Since the function $XIC_i$ is, as noted above, in fact a discrete function, this "integration" really is a summing:

$$c_{i,j} = \Sigma_{\Delta rt, j} XICi(rt). \quad (2)$$

Therein, $c_{i,j}$ denotes the characteristic value for the $i^{th}$ mass variable interval 424 and for the $j^{th}$ time variable interval 426. Thus, as a result of process step 414, a matrix of characteristic values $c_{i,j}$ is generated, which is a characteristic sample profile characterizing the sample comprising the at least one compound, and which is a "reduced data set" for the original raw data set (i.e. the signal I).

In a following, optional process step, step 116 in FIG. 1, additional parameters may be obtained from the extracted signal $XIC_i$ in FIG. 6. Alternatively or additionally, the characteristic parameters $c_{i,j}$, as generated according to the method described above, may be transformed, e.g., by normalizing or any other transformation. As an example, the characteristic parameter $c_{i,1}$ for the extracted signal XICi depicted in FIG. 6 is symbolically denoted by the black area in FIG. 6, which is the area underneath the extracted signal XICi 510 in FIG. 6 in the first time variable interval TS 1. Since this area strongly depends on the settings of the experimental system 210 as depicted in FIG. 2, it may, e.g., be normalized to the overall signal height. Thus, the area obtained by using formula (2), generating the characteristic parameters $c_{i,j}$, may be, in step 116, divided by the height of the highest peak 512 in time variable interval 426. Thus, the characteristic parameters $c_{i,j}$ may be replaced by new characteristic parameters $c_{i,j}'$, which are the characteristic parameters $c_{i,j}$, divided by the height of the peak 512. Thereby, the characteristic parameters are "normalized" and become nearly independent of the experimental settings of the experimental system 210.

In FIG. 7, for comparison, a "traditional" peak detection algorithm is shown as opposed to the method of the present invention. As depicted in FIG. 7, for using a peak detection algorithm, first of all, the peak 512 has to be detected. Afterwards, in this example of a peak detection algorithm, a characteristic value is obtained by integrating the highest peak 512 of the time variable interval TS 1, whereby, as boundaries for the integration, minima neighboring to the highest peak 512 are used. As can be seen, these integration boundaries strongly depend on the nature of the peaks neighboring to the highest peak 512, and, thus, the uncertainty of the method according to FIG. 7 is rather high. Further, in many cases, especially when neighboring peaks are very close, an integration of the peak 512 may fail completely, since the integration boundaries are undefined. This leads to "missing values" in the characteristic sample profile. Using the method according to the invention depicted in FIG. 6, the risk of "missing values" is significantly reduced, allowing for a complete evaluation of the three-dimensional first set of data for each sample. Further, the method according to the invention depicted in FIG. 6 is not restricted to peaks, which means that other characteristic features of the extracted signal XIC 510 contribute to the characteristic values $c_{i,j}$, such as "shoulders" or "hills".

The process steps 118, 120, and 122 in FIG. 1 denote additional steps of evaluation of the characteristic sample profile as generated by the method described above. Thus, in step 118, a number of samples may be analyzed and/or combined by statistical evaluation (step 118). In this optional process step, e.g., a median, a mean value, a standard deviation (SD), a relative standard deviation (RSD) or other statistical values for the samples may be generated and the data might be transformed e.g. by a logarithmic transformation. Thus, several samples may be compared and/or combined, in order to obtain statistical information of the samples.

In the optional process step 120 (FIG. 1), the statistical data may be visualized, in order to visualize the distribution of certain characteristic values over a large number of samples. Thus, e.g., samples and/or characteristic values which deviate from a mean value by more than a predetermined "allowable" deviation may be eliminated from the data set. FIGS. 8 and 9 show the results of such a quality control for 48 blood plasma samples from untreated and medicated rats (several different treatments). In FIG. 8 the scores of a principal component analysis with the Hotelling $T^2$ ellipse (at the 0.95 confidence interval) as limit for defining a multivariate outlier are shown. In this case none of the samples falls outside the ellipse i.e. based on this test there are no obvious multivariate outliers. In FIG. 9 the loadings for 9005 variables used in the same principal component analysis as in FIG. 8 are visualised to inspect the contribution of the different variables to the sample separation. Variables having a strong influence on the statistical separation of the samples are characterised by large absolute values. These variables are candidates for the use as classifiers and thus they can be focused on in further statistical analysis.

In a further optional process step, step 122 in FIG. 1, the statistical results of the previous process steps for the characteristic values of the sample or the plurality of samples are compared to reference values, e.g., reference values of a (real or virtual) reference sample. Thus, e.g., by generating the ratio between any certain characteristic value (which may, as indicated above, e.g., be a mean value of a plurality of samples) the likelihood for the presence, absence or amount of a certain chemical compound within the sample or the plurality of samples may be obtained. Thus, a quantitative and/or qualitative analysis of the sample or plurality of samples may be performed. FIGS. 10 and 11 show examples of results from step 122. Data from blood plasma samples from untreated and medicated rats (two different medications, subset of the treatments used in the analysis in FIG. 8, result visualised for 33 samples) were subjected to a principal component analysis (PCA) that was based on a variable pre-selection (52 variables) derived from an anova analysis (as part of step 118; note: alternatively the loadings information shown in FIG. 9 could also have been used for variable pre-selection as suggested above). As can be seen in FIG. 10, all three different treatments can be separated and the key variables driving this separation can be identified (FIG. 11).

The results obtained by the aforementioned comparisons are indicative as to whether a sample is identical to a reference sample. However, the analysis may in some cases merely give a first estimation and further steps in which the precise sample composition is quantitatively and/or qualitatively determined are required in addition. Preferably, such comparisons may be used in metabolomics, e.g., for the investigation of metabolic changes being the result of exogenous influences. The methods of the present invention, advantageously, can be used to evaluate high throughput screens for compounds which effect the metabolome of an organism, such as potential drugs or potentially toxic compounds. In said high throughput screens thousands of compounds are screened in order to determine suitable candidates, e.g., for drug development or to identify toxic compounds. A comprehensive metabolome analysis would yield enormous amounts of data which can not be handled, e.g. compared to each other, in a time efficient and/or cost efficient manner. The methods described herein allow to pre-select suitable candidates which effect the metabolome by using a dimensionally reduced, less complex set of data. Said pre-selection can be done in a less time- and cost-effective manner. The pre-selected candidates may then be investigated further for the desired properties.

The results of the process steps described above, such as the characteristic values for each sample, may be stored within the computer system 220 in FIG. 2. This computer system 220 may comprise several separate computers, and may comprise one or more databases. Thus, separate computers for controlling the experimental systems 214, 216 and for evaluation of the experimental data may be used. Thus, the experimental data obtained by the process steps described above may be evaluated on a separate computer system.

All references cited throughout this specification are herewith incorporated by reference in their entireties and with respect to the specific disclosure content referred to in the specification herein above.

The invention claimed is:

1. A method for characterizing a sample containing at least one compound, wherein a computer system controls a time resolved detection system and a mass resolved detection system, the method comprising:
   a) generating, with the computer system, a three-dimensional first set of data by analyzing the sample using at least one time resolved separation technique and at least one mass resolved separation technique, wherein the first set of data comprises at least one signal I as a function of a mass variable over a first range of measurement and of a time variable over a second range of measurement, the mass variable being derived from a mass of the sample, and the time variable being representative of a progression of time for the time resolved separation technique;
   b) dividing, with the computer system, the first range of measurement into at least two mass variable intervals and selecting an extracted signal for each mass variable interval, wherein the extracted signal is a function of the time variable; then
   c) dividing, with the computer system, the second range of measurement into at least two variable time intervals and selecting at least one characteristic value for each time variable interval and for each extracted signal, whereby a characteristic sample profile is generated, the characteristic sample profile comprising the at least one characteristic value as a function of the respective time variable interval and of the respective mass variable interval.

2. The method according to claim 1, wherein selecting the extracted signal for each mass variable interval includes at least one of:
   integrating the signal I over the mass variable interval;
   summing the signal I over the mass variable interval;
   averaging the signal I over the mass variable interval;
   selecting the signal I at one of the interval boundaries of the mass variable interval; and
   selecting the maximum or minimum value of the signal I over the mass variable interval.

3. The method according to claim 1, wherein selecting at least one characteristic value for each time variable interval includes at least one of:
   integrating the extracted signal over each time variable interval;
   summing the extracted signal over each time variable interval;
   averaging the extracted signal over each time variable interval;
   selecting the extracted signal at one of the interval boundaries of the time variable interval; and
   selecting the maximum or minimum value of the extracted signal over the time variable interval.

4. The method according to claim 1, further comprising:
   d) comparing, with the computer system, the characteristic sample profile of the sample with at least one of a characteristic sample profile of a second sample and a reference sample profile.

5. The method according to claim 4, wherein comparing the characteristic sample profile of the sample includes comparing a characteristic value of the characteristic sample profile with at least one of a corresponding characteristic value of the second sample profile and a corresponding characteristic value of the reference sample profile.

6. The method according to claim 4, wherein comparing the characteristic sample profile of the sample includes using at least one of:
   a pattern recognition algorithm;
   a statistical test algorithm; and
   a multivariate algorithm.

7. The method according to claim 1, wherein dividing the second range of measurement includes using a peak detection algorithm to detect peaks in the extracted signal within each time variable interval.

8. The method according to claim 1, wherein the at least one time resolved separation technique comprises chromatography.

9. The method according to claim 8, wherein the chromatography comprises at least one of:
   gas chromatography;
   liquid chromatography;
   capillary electrophoresis;
   thin layer chromatography; and
   affinity chromatography.

10. The method according to claim 1, wherein the at least one mass resolved separation technique comprises mass spectrometry.

11. The method according to claim 10, wherein the mass spectrometry comprises at least one of:
   magnetic sector field mass spectrometry;
   time-of-flight mass spectrometry;
   quadrupole mass spectrometry; and
   ion trap mass spectrometry.

12. The method according to claim 1, wherein the at least one time variable interval, $\Delta rt$, is chosen according to the following formula:

$$R_{rt} \leq \Delta rt \leq L_{rt},$$

wherein $R_{rt}$ denotes one of a cycle time of the at least one time resolved separation technique or a minimum time interval within which two distinct peaks are resolvable, and wherein $L_{rt}$ denotes a full range of chromatographic measurement.

13. The method according to claim 1, wherein said compound is a metabolite.

14. The method according to claim 1, wherein at least one characteristic value of a sample profile is recorded in a data base.

15. The method according to claim 1, wherein the mass variable is derived from one of a mass or a mass-to-charge ratio.

16. A method for characterizing a sample containing at least one compound, wherein a computer system controls a time resolved detection system and a mass resolved detection system, the method comprising:
   a) generating, with the computer system, a three-dimensional first set of data by analyzing the sample using at least one time resolved separation technique and at least one mass resolved separation technique, wherein the first set of data comprises at least one signal I as a function of a mass variable over a first range of measurement and of a time variable over a second range of measurement;
   b) dividing, with the computer system, the first range of measurement into at least two mass variable intervals and selecting an extracted signal for each mass variable interval, wherein the extracted signal is a function of the time variable; then
   c) dividing, with the computer system, the second range of measurement into at least two variable time intervals and selecting at least one characteristic value for each time variable interval and for each extracted signal, whereby a characteristic sample profile is generated, the characteristic sample profile comprising the at least one characteristic value as a function of the respective time variable interval and of the respective mass variable interval; and
   d) comparing, with the computer system, the characteristic sample profile of the sample with at least one of a characteristic sample profile of a second sample and a reference sample profile;
the method further comprising at least one of:
   determining, with the computer system, whether the sample and at least one of the second sample and the reference sample are likely to be identical; and
   determining, with the computer system, whether the sample and at least one of the second sample and the reference sample are likely to include one or more identical or similar compounds.

17. The method according to claim 16, further comprising, if the sample and the second sample or the reference sample are likely to be identical or are likely to comprise one or more identical or similar compound, comparing, with the computer system, a relevant portion of the three-dimensional first set of data of the sample to a relevant portion of a three-dimensional first set of data of at least one of the second sample and of the reference sample.

18. A method for characterizing a sample containing at least one compound, wherein a computer system controls a time resolved detection system and a mass resolved detection system, the method comprising:
   a) generating, with the computer system, a three-dimensional first set of data by analyzing the sample using at least one time resolved separation technique and at least one mass resolved separation technique, wherein the first set of data comprises at least one signal I as a function of a mass variable over a first range of measurement and of a time variable over a second range of measurement;
   b) dividing, with the computer system, the first range of measurement into at least two mass variable intervals and selecting an extracted signal for each mass variable interval, wherein the extracted signal is a function of the time variable; then
   c) dividing, with the computer system, the second range of measurement into at least two variable time intervals and selecting at least one characteristic value for each time variable interval and for each extracted signal, whereby a characteristic sample profile is generated, the characteristic sample profile comprising the at least one characteristic value as a function of the respective time variable interval and of the respective mass variable interval;
wherein a length of each mass variable interval, $\Delta m$, is chosen according to the following formula:

$$R_{mz} \leq \Delta m < L_{mz},$$

wherein $R_{mz}$ denotes a mass peak width of the at least one mass resolved separation technique, and wherein $L_{mz}$ denotes a full length of a first range of measurement.

19. The method according to claim 18, wherein the length of each mass variable interval, $\Delta m$, is chosen to be 1 atomic mass unit (amu).

* * * * *